US009610389B2

(12) United States Patent
Ruland

(10) Patent No.: US 9,610,389 B2
(45) Date of Patent: Apr. 4, 2017

(54) SELF-CONTAINED CRYOTHETRAPY AND SUCTION SYSTEM

(75) Inventor: Robert T. Ruland, Portsmouth, VA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 979 days.

(21) Appl. No.: 13/406,233

(22) Filed: Feb. 27, 2012

(65) Prior Publication Data

US 2012/0220960 A1    Aug. 30, 2012

Related U.S. Application Data

(60) Provisional application No. 61/464,215, filed on Feb. 28, 2011.

(51) Int. Cl.
  *A61F 7/00*     (2006.01)
  *A61M 1/00*    (2006.01)
  *A61F 7/02*     (2006.01)

(52) U.S. Cl.
  CPC .............. *A61M 1/0088* (2013.01); *A61F 7/02* (2013.01); *A61F 2007/0056* (2013.01); *A61F 2007/0212* (2013.01); *A61F 2007/0219* (2013.01); *A61F 2007/0231* (2013.01); *A61F 2007/0239* (2013.01); *A61F 2007/0257* (2013.01); *A61F 2007/0258* (2013.01); *A61M 2205/3606* (2013.01)

(58) Field of Classification Search
  CPC .................. A61F 7/02; A61F 2007/056; A61F 2007/0212; A61F 2007/0219; A61F 2007/0231; A61F 2007/0239; A61F 2007/0257; A61F 2007/0258; A61F 2007/3606
  See application file for complete search history.

(56) References Cited

U.S. PATENT DOCUMENTS

| 4,969,880 A | 11/1990 | Zamierowski |
| 5,100,396 A | 3/1992 | Zamierowski |
| 5,636,643 A | 6/1997 | Argenta et al. |
| 5,645,081 A | 7/1997 | Argenta et al. |
| 6,071,267 A | 6/2000 | Zamierowski |
| 7,004,915 B2 | 2/2006 | Boyton et al. |
| 7,611,500 B1 | 11/2009 | Lena et al. |
| 2009/0240216 A1* | 9/2009 | Hannigan et al. ............ 604/290 |
| 2010/0095641 A1* | 4/2010 | Ruetenik ........................ 54/82 |
| 2010/0179493 A1 | 7/2010 | Heagle |
| 2011/0213287 A1 | 9/2011 | Lattimore |

* cited by examiner

*Primary Examiner* — Leslie Deak
*Assistant Examiner* — Kai Weng
(74) *Attorney, Agent, or Firm* — Ning Yang; Albert M. Churilla; Diane P. Tso

(57) ABSTRACT

A method for treating wounds, comprised of the application of reduced pressure to a wound site and alteration of the temperature over said wound. A system for wound healing, comprising: a substantial impermeable drape sized to cover and enclose the wound creating a reservoir and adapted to maintain reduced pressure at the site of the wound; a sterilizable porous cooling pad incorporated into a wound sponge adapted to provide localized cooling to said wound, said cooling pad located between said wound and said cover or over the drape; a reduced pressure supply mechanism capable of providing subatmosphere pressure over said wound site.

30 Claims, 8 Drawing Sheets

Figure 1:
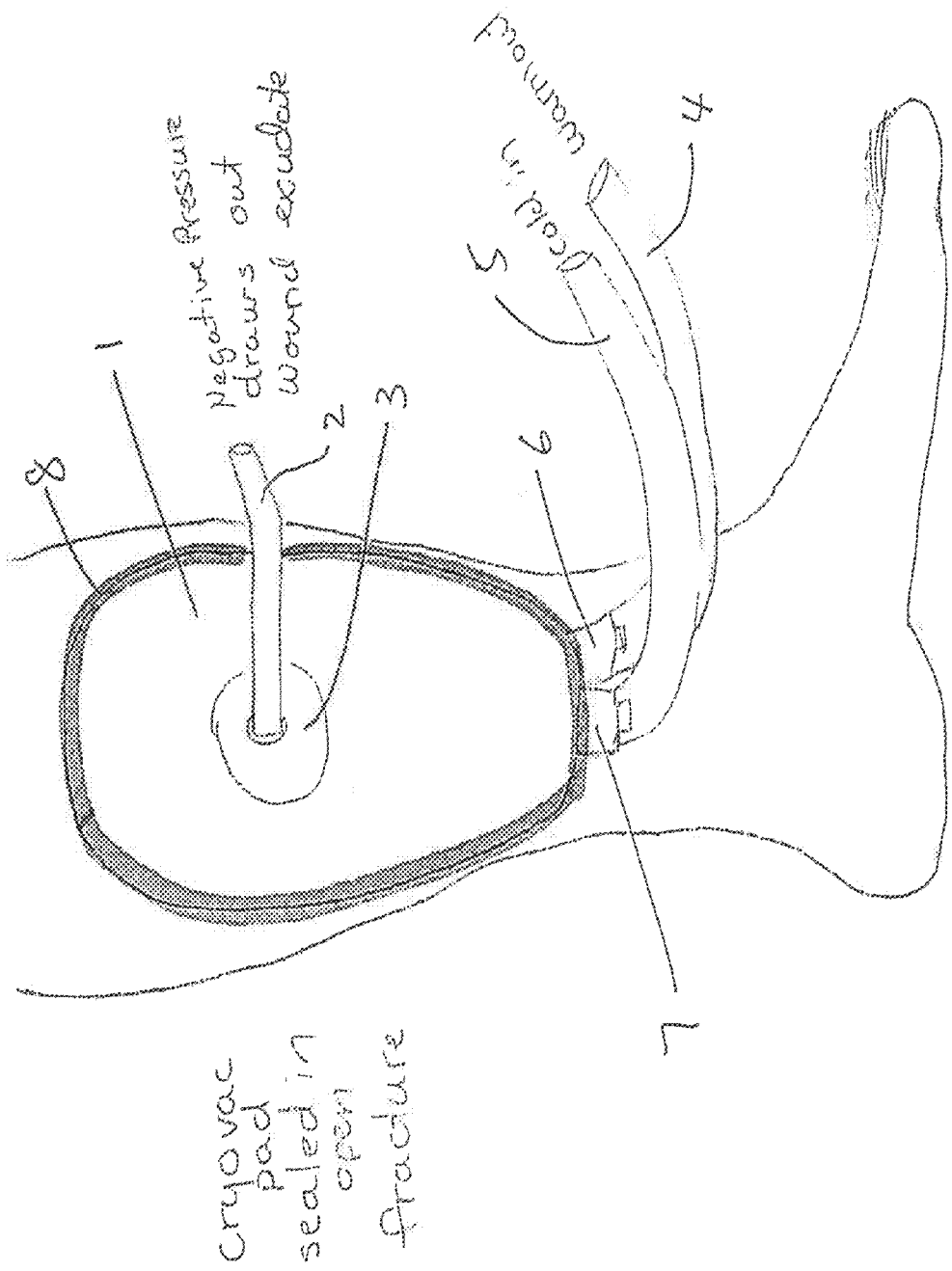

Group I: inoculation and cooling; Group II inoculation without cooling; Group III: no inoculation and no cooling Group I: inoculation and cooling; Group II inoculation without cooling Group I: inoculation and cooling; Group II inoculation without cooling; Group III: no inoculation and no cooling

SELF-CONTAINED CRYOTHETRAPY AND SUCTION SYSTEM

CROSS-REFERENCE TO RELATED APPLICATIONS

This application claims the benefit of U.S. Provisional Application No. 61/464,215 filed Feb. 28, 2012, the entirety of which is hereby incorporated by reference.

BACKGROUND

Embodiments of the present invention relate generally to the treatment of a wound using a combined method consisting of negative (or reduced) pressure therapy and localized cooling. More specifically, the present invention relates to a system and a wound treatment method, which provides negative pressure and localized cooling at an open wound site while allowing continuous drainage of exudates from the wound.

Orthopedic extremity trauma accounts for 65 percent of combat wounds, over half of which are penetrating soft-tissue wound. Treatment of open wounds has long been a troublesome area in the practice of medicine. Some wounds are sufficiently large or infected that they are unable to heal spontaneously. In these complex cases, infection rates are directly related to the severity of the injury and the degree of contamination.

A recently published guideline for prevention of infection after combat-related injuries recommends rapid transport to higher level of care, immediate stabilization of fractures, early administration of antibiotics, repeated irrigation and debridement of wounds, and negative pressure wound therapy in the combat zone [1]. Even with these advancements in management of combat-related injuries, infections are still relatively common and morbid; resulting in delayed wound healing, multiple surgeries and administration of long term intravenous antibiotics. If unsuccessfully managed, these wounds can progress to chronic infections, and possibly lead to amputations of previously salvageable limbs.

The goals of current treatment protocol for infected wounds are simple:
 a. minimize bacterial numbers through surgical debridement of contaminated tissue, and
 b. alter the wound environment to directly kill bacteria or inhibit replication, usually via the administration of antibiotics.

With the increasing prevalence of multi-drug resistant organisms (14, 15), further advancements in wound care need to be explored.

It is well known that there are optimal temperatures at which bacteria grow more readily. Deviations from this ideal temperature, both warming and cooling, can slow bacterial growth. For example, localized temperature elevation has been shown to decrease bacterial load in wounds (2, 3, 4). Localized cooling has been also shown to be beneficial in orthopedics by providing analgesic and anti-inflammatory properties, resulting in a decreased need for narcotics, less quadriceps inhibition, and a quicker recovery of function as compared to controls (9-13). However, total body hypothermia has been shown to hinder wound healing (5, 6). Prior research has shown that total body hypothermia is detrimental to wound healing, while others have demonstrated that a 3° to 6° C. drop in core temperature can be harmful in the setting of infection (4-8). With this level of systemic hypothermia, the host immune response is blunted, potentially leading to accelerated bacterial growth and overwhelming sepsis. The effects of this intervention on mortality in sepsis are still controversial (4, 7, 8). The effectiveness of localized cooling on infected wounds has not been studied.

Closure of surface wound involves inward migration of epithelial and subcutaneous tissue adjacent to the wound. This migration is ordinarily assisted through the inflammatory process, whereby blood flow is increased and various functional cell types are activated. Through the inflammatory process, blood flow through damaged or broken vessels is stopped by capillary level occlusion. Thereafter, cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but also are also less able to successfully fight bacterial infection. As a result, the body is less able to naturally close the wound.

Such difficult wounds were commonly addressed only through the use of sutures or staples. Although still widely practiced and sometimes effective, such mechanical closure techniques suffer a major disadvantage in that they produce tension on the skin tissue adjacent the wound. In particular, the tensile force required in order to achieve closure using sutures or staples may cause very high localized stresses at the suture or staple insertion point. These stresses can result in the rupture of the tissue at the insertion points, which eventually cause wound dehiscence and additional tissue loss.

Furthermore, some wounds harden and inflame to such a degree due to infection that closure by stapling or suturing is not feasible. Wounds not reparable by suturing or stapling generally require prolonged hospitalization, with its attendant high cost, and major surgical procedures, such as grafts of surrounding tissues. Examples of wounds not readily treatable with staples or suturing include large, deep, open wounds; decubitus ulcers; ulcers resulting from chronic osteomyelitis; and partial thickness burns that subsequently develop into full thickness burns.

As a result of these and other shortcomings of mechanical closure devices, one particular technique for promoting the body's natural healing process may be described as negative pressure wound therapy (NPWT). This technique involves the application of a reduced pressure, e.g. sub-atmospheric, to a localized reservoir over a wound. Sub-atmospheric pressure has been found to assist in closing the wound by promoting blood flow to the area, thereby stimulating the formation of granulation tissue and the migration of healthy tissue over the wound. This technique has proven effective for chronic or non-healing wounds, but has also been used for other purposes such as post-operative wound care.

In practice, the application to a wound of negative gauge pressure, commercialized under the designation "Vacuum Assisted Closure" (or "V.A.C® therapy). The related treatment methods and devices have been described in U.S. Pat. No. 4,969,880 issued on Nov. 13, 1990 to Zamierowski, as well as its continuations and continuations in part, U.S. Pat. No. 5,100,396, issued on Mar. 31, 1992, U.S. Pat. No. 5,261,893, issued Nov. 16, 1993, and U.S. Pat. No. 5,527,293, issued Jun. 18, 1996. Further improvements and modifications of the vacuum induced healing process are also described in U.S. Pat. No. 6,071,267, issued on Jun. 6, 2000 to Zamierowski and U.S. Pat. Nos. 5,636,643 and 5,645,081 issued to Argenta et al. on Jun. 10, 1997 and Jul. 8, 1997 respectively, U.S. Pat. No. 7,004,915, issued to Boynton et al. on Feb. 28, 2006, U.S. Pat. No. 7,611,500, issued to Lina et al. on Nov. 3, 2009 and US Patent publication No. 20110213287 to Lattimore et al and US Patent publication No. 20090204085 to Biggie et al.

The general NPWT protocol provides for covering the wound with a flexible cover layer such as a polymeric film, for example, to establish a vacuum reservoir over the wound where a reduced pressure may be applied by individual or cyclic evacuation procedures. To allow the reduced pressure to be maintained over time, the cover layer may include an adhesive periphery that forms a substantially fluid tight seal with the healthy skin surrounding the wound.

Although some procedures may employ a micro-pump contained within the vacuum reservoir, most NPWT treatments apply a reduced pressure using an external vacuum source. Fluid communication must therefore be established between the reservoir and the vacuum source. To this end, a fluid port is coupled to the cover layer to provide an interface for an exudate conduit extending from the external vacuum source.

The embodiments of the present invention incorporate localized cooling therapy into current NPWT treatment system to stimulate and aid the treatment of infected or other open wounds.

DETAILED DESCRIPTION OF DRAWINGS

FIG. 1: Illustrative view of an embodiment of the self-contained closed cyro-vac system.

Figure 2:
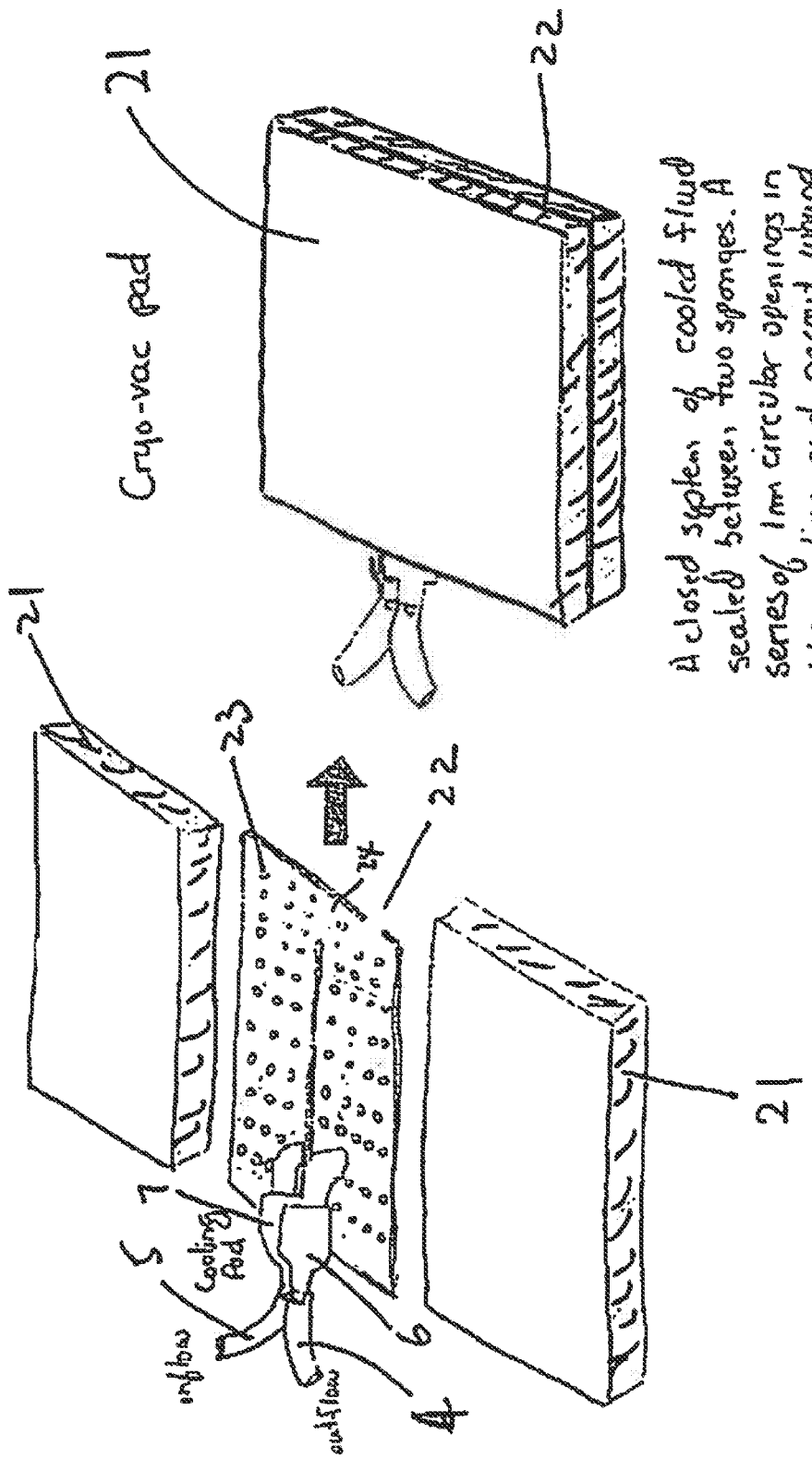

FIG. 2: Illustrative view of an embodiment of the cooling pad.

Figure 3:
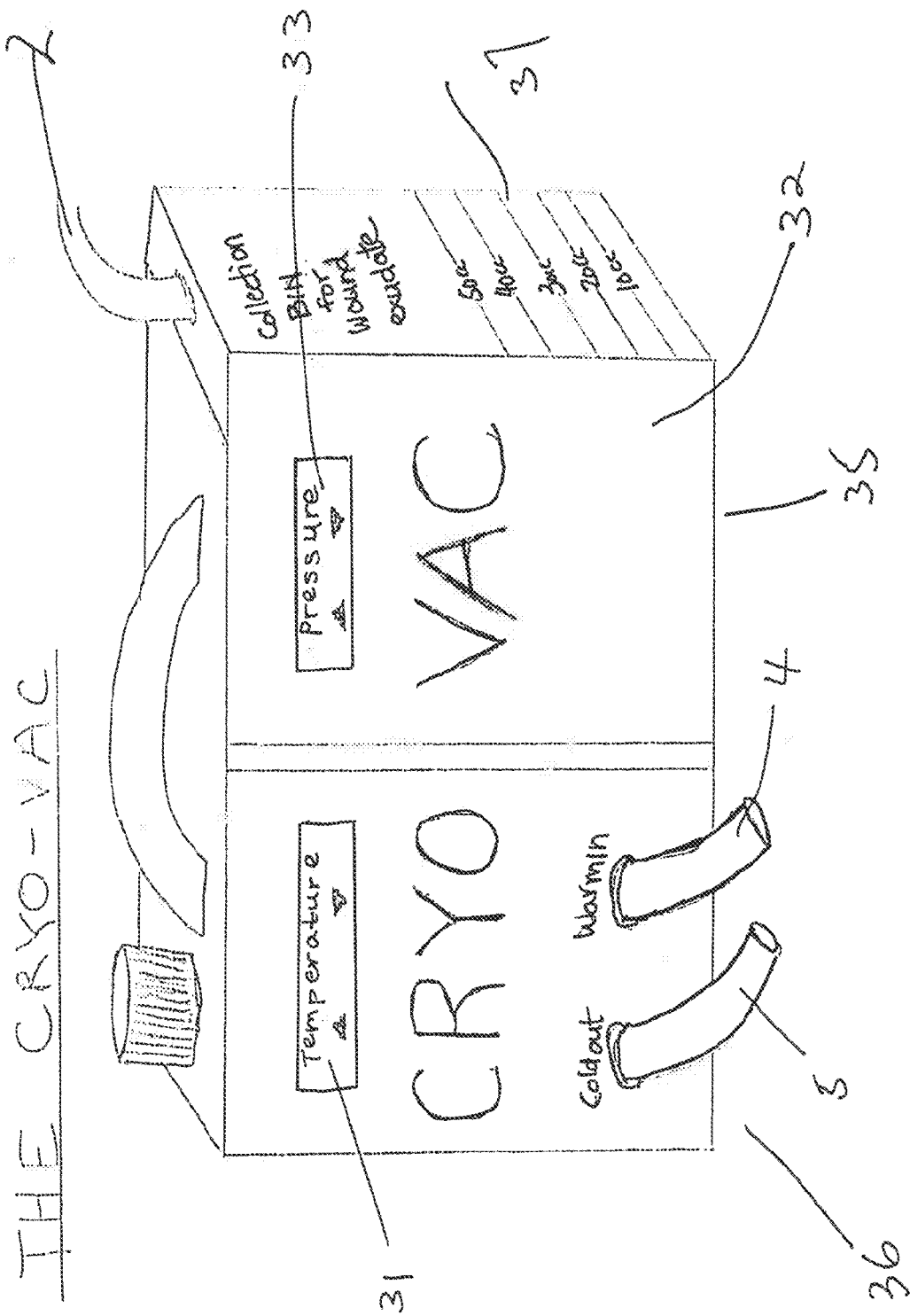

FIG. 3: Illustrative view of an embodiment of the cryo-vac machine

Figure 4:
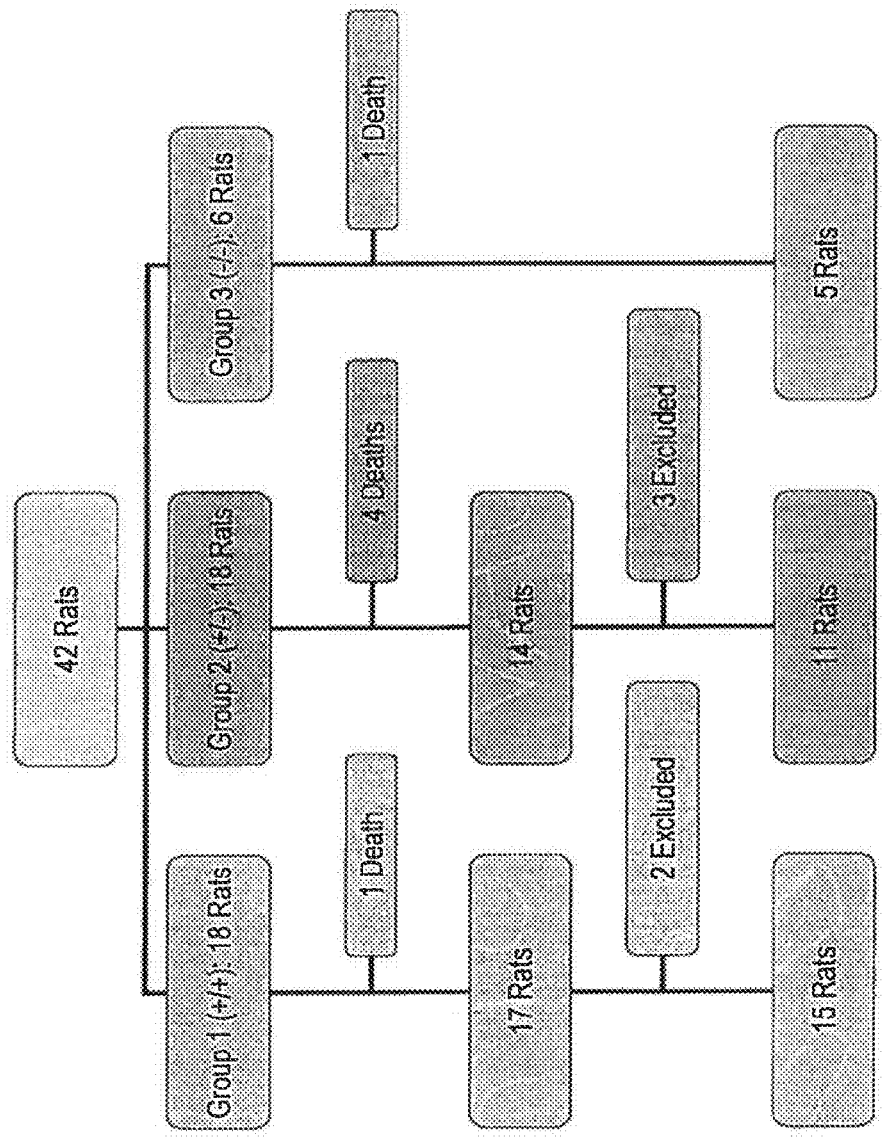

FIG. 4: Animal Survival of the localized cooling experiment.

Figure 5:
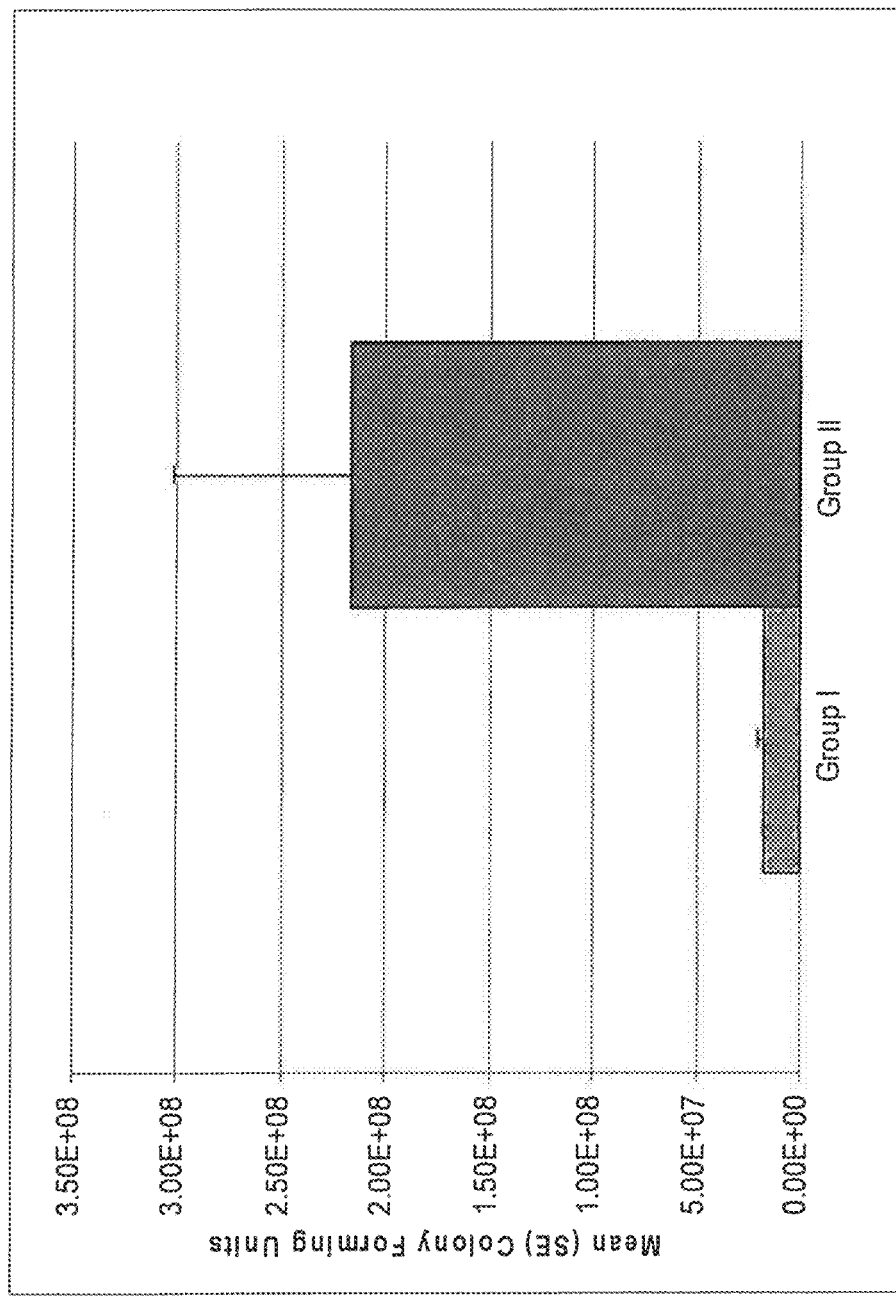

FIG. 5: Bar graph showing mean colony forming units (with standard error bars) 8 hours after inoculation. Group I (cooled) had significantly lower colony forming units than Group II (control). (p=0.041)

Figure 6:
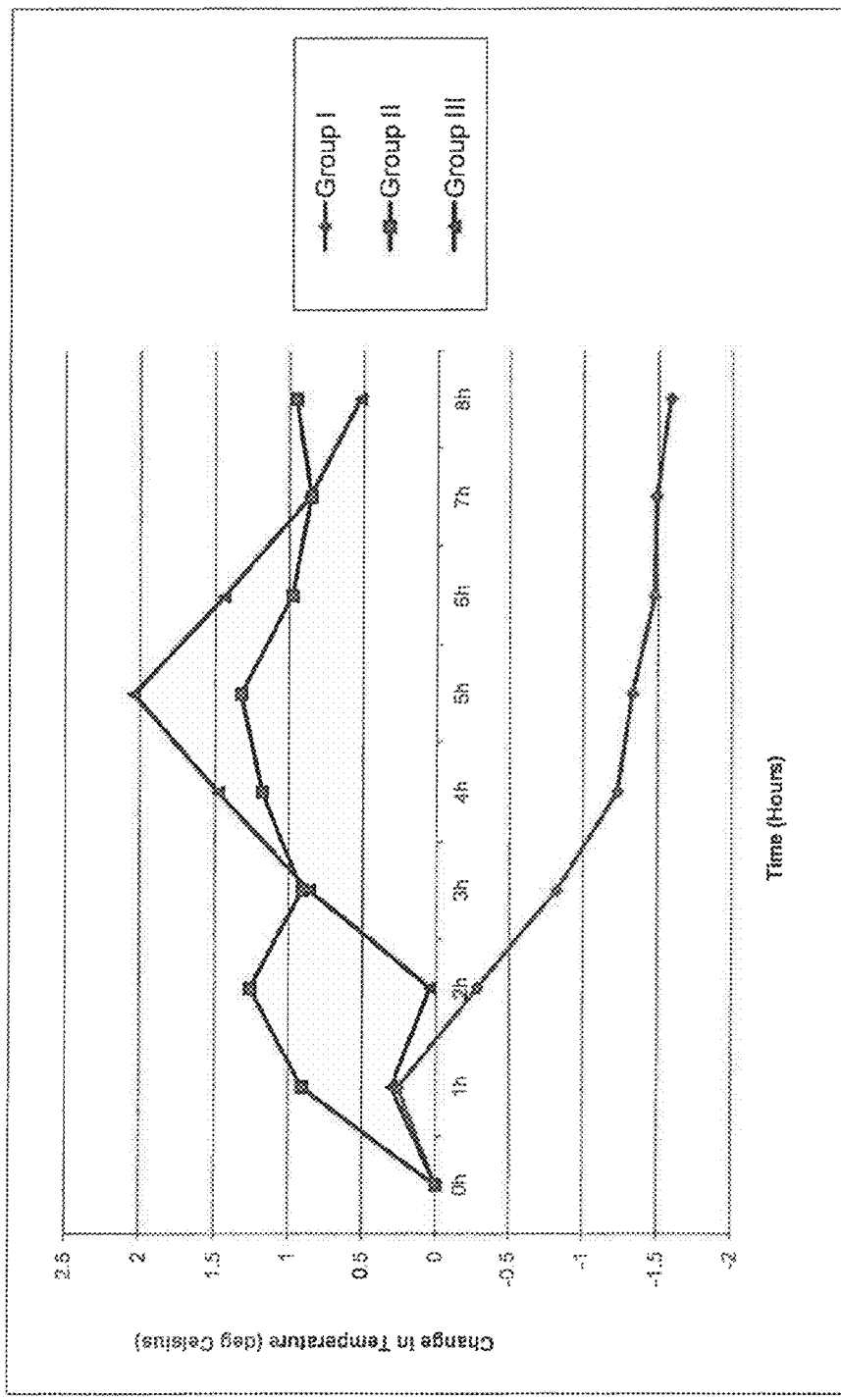

FIG. 6: Temperature curve demonstrating hourly changes from baseline of mean core temperatures. The difference between Group I and Group II was statistically significant at all time points (p<0.01). The difference between Group I and baseline was statistically significant from hours 3 to 8 (p<0.01).

Figure 7:
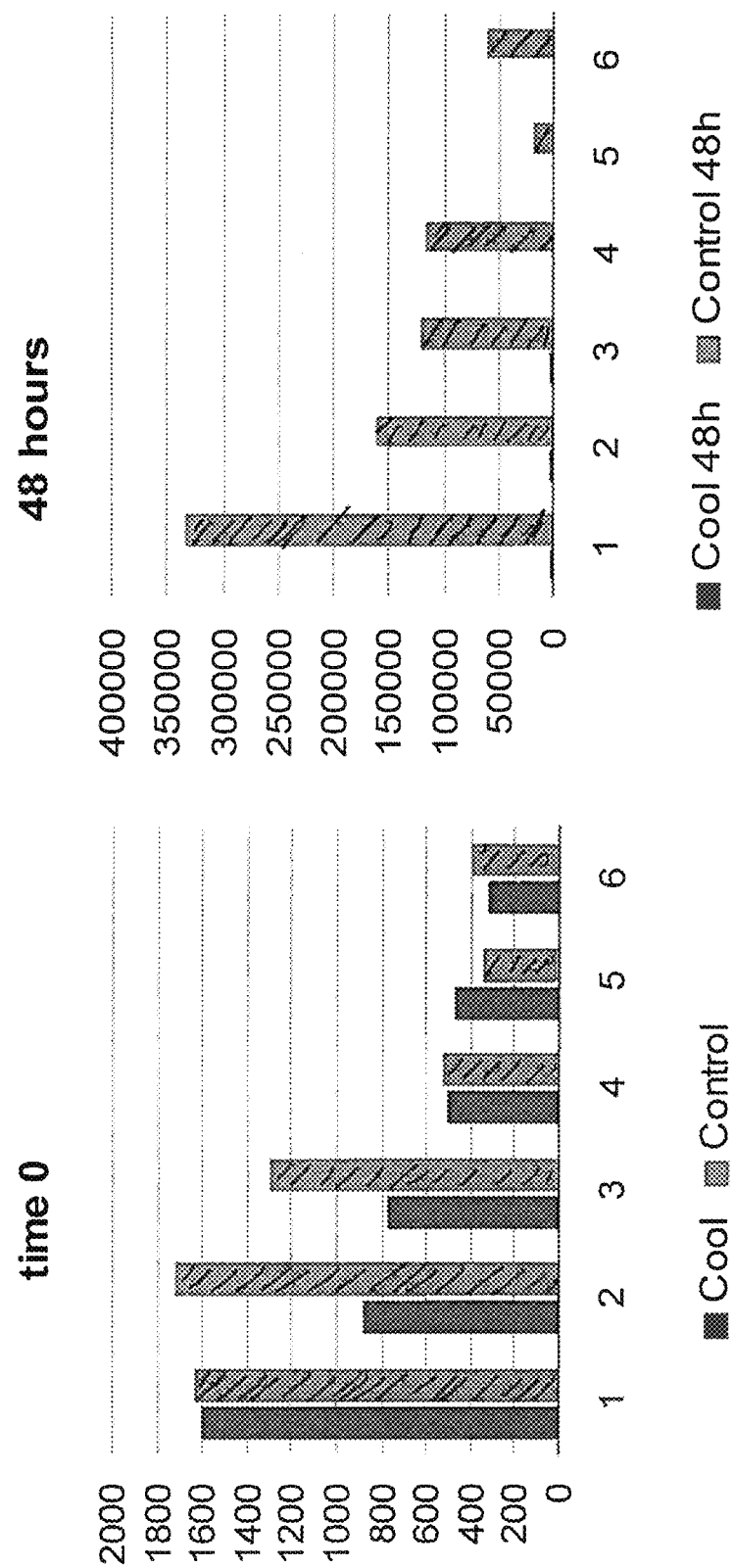

FIG. 7: comparison of photon emission from bioluminescent bacteria in an open fracture model in goats before and 48 hours after bacterial inoculation between the control limb and treatment limb, which received localized cooling, (p<0.03).

Figure 8:
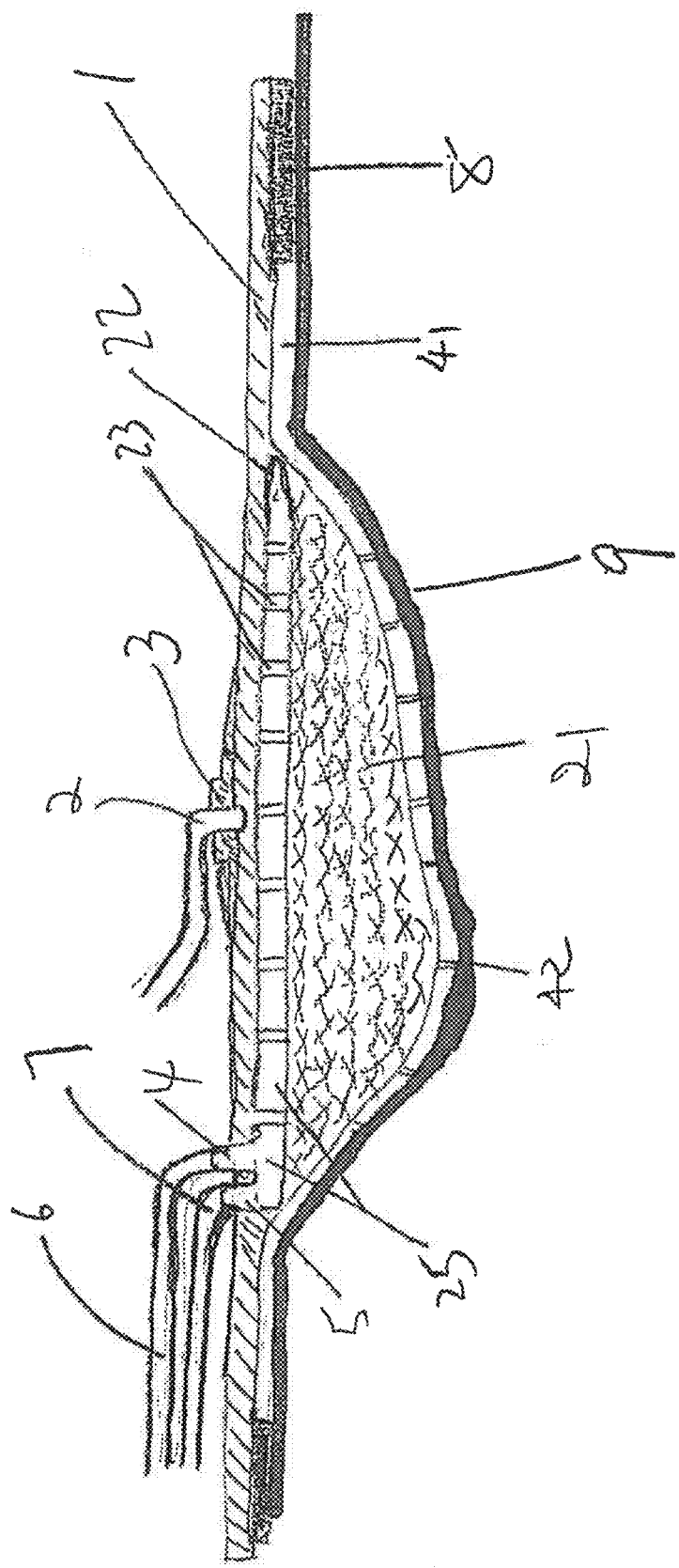

FIG. 8: Cross-sectional view of an embodiment of the invention.

DETAILED DESCRIPTION OF THE INVENTION

Although those of ordinary skill in the art will readily recognize many alternative embodiments, especially in light of the illustrations provided herein, this detailed description is exemplary, the scope of which is limited only by the claim that are drawn hereto.

The term "wound" as used herein in addition to having its broad ordinary meaning, includes any body parts of a patient that may be treated using reduced pressure. Wounds and/or wound sites include but are not limited, open wounds, pressure sores, ulcers, and burns. Open wounds and/wound sites may also include incisions, or other openings, tears, or fistulas, for example, in the abdominal or peritoneal cavity. Treatment of such wounds can be performed using negative pressure wound therapy, wherein a reduced or negative pressure can be applied to the wound to facilitate and promote healing of the wound.

The wound therapy system of the present disclosure promotes healing of a wound via the use of a reduced or negative (subatmospheric) pressure mechanism as well as a localized cooling pad, and collection storage. Generally, the reduced pressure mechanism applies subatmospheric pressure to the wound effectively removing wound fluids or exudates captured within the boundary of a composite wound dressing or impermeable cover. It will also increase blood flow to the wound bed enhancing cellular stimulation of epithelial and subcutaneous tissue. The localized cooling pad reduces the temperature at the wound site deterring the growth of harmful bacteria while providing analgesia. This wound therapy system may be entirely portable, i.e., it may be worn or carried by the subject such that the subject may be completely ambulatory during the therapy period. The wound therapy system including the subatmospheric pressure mechanism and components thereof may be entirely reusable or may be entirely disposable after a predetermined period of use or may be individually disposable whereby some of the components are reused for a subsequent therapy application.

In an embodiment, a system to promote the healing of a wound, reduce the proliferation of bacteria, and provide analgesia, comprising:
  (a) a flexible drape sized to seal in a wound site, and adapted to maintain a substantial airtight watertight reservoir over the wound site;
  (b) a cooling pad placed over the wound site, and adapted to reduce the temperature of the wound site;
  (c) a reduced pressure mechanism including
    (i) a control unit disposed within a housing, the control unit including a vacuum source; and
    (ii) a collection storage having an interior wall defining an internal chamber in fluid communication with the vacuum source of the reduced pressure mechanism through a vacuum port and with the reservoir for collecting exudates removed from the wound site under influence of the vacuum source.

Referring to FIG. 1. a wound is covered by a flexible drape 1, such as a polymeric film. The drape 1 can be at least substantial impermeable, such that at least a partial negative pressure may be maintained at the wound site. Suitable materials for the drape 1 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include TRANSEAL™ available from DeRoyal and OP SITE™ available from Smith & Nephew. In order to aid patient comfort and avoid skin maceration, the drapes in certain embodiments are at least partly breathable, such that water vapor is able to pass through without remaining trapped under the dressing. An adhesive layer 8 may be provided on at least a portion the underside of the drape 1 to secure the drape to the skin of the patient, although certain embodiments may instead use a separate adhesive or adhesive strip. Optionally, a release layer may be disposed over the adhesive layer to protect it prior to use and to facilitate handling the drape 1; in some embodiments, the release layer may be composed of multiple sections. A seal between the drape and the healthy skin surrounding the wound creating a substantial airtight, fluid tight reservoir over the wound site 9 (FIG. 8).

Once a substantial airtight watertight reservoir is established over the wound site 9 (FIG. 8) underneath the drape 1, a reduced pressure may be applied by individual or cyclic evacuation procedures. The reduced pressure is applied via a reduced pressure mechanism 35 including a control unit 33 disposed within a housing, the control unit 33 including a vacuum source 32; and a collection storage 37 having an interior wall defining an internal chamber in fluid communication with the vacuum source 32 of the reduced pressure mechanism and with the reservoir through a vacuum port for collecting exudates removed from the wound site under influence of the vacuum source 32.

Although some procedures may employ a micro-pump contained within the reservoir, most NPWT treatments apply a reduced pressure using an external vacuum source 32 (FIG. 3). One example of a suitable pump is the Renasys EZ pump available from Smith & Nephew. Fluid communication must therefore be established between the reservoir and the vacuum source 32. To this end, a connector 3 (see FIG. 1, FIG. 8) is coupled to the drape 1 to provide an interface for a tubing 2 extending from drape 1 to the external vacuum source 32. The flexible tubing 2 may be made with materials such as plastic and rubber. Pressure within the reservoir is maintained at about 2 in. Hg below atmospheric pressure to about 7 in. Hg below atmospheric pressure. The connector 3 may be resealable allowing the drape to remain airtight when tubing 2 is removed. A segment of tubing may be embedded underneath said drape. The tubing may also be directly connected to the drape without using a connector 3.

Referring to FIG. 8, a cooling pad, amenable to sterilization, 22 is placed over the wound to reduce the temperature of the wound site 9, which can be an ice or gel Pac. The cooling pad may be placed between the wound and the impermeable cover or affixed over the wound outside the impermeable cover using adhesive, tape, elastic or Velcro etc. In one embodiment, as shown in FIGS. 2 and 8, the cooling pad 22 is a pouch that has a continuous outer surface 24, forming an inner chamber 25. The inner chamber 25 is connected with a coolant supply via an inlet port 7 and an outlet port 6. The cooling pad is designed to be at least partially porous, allowing aspired exudates from the wound to pass through the cooling pad. For example, small opening, such as perforations, channels or slits 23, may be formed through the cooling pad 22 to allow fluid and exudates to be suctioned from the wound. The inner chamber 25 of the cooling pad may be designed to allow coolant to enter the pad through inflow tube 5 via the inlet 7, and circulate throughout the entire inner chamber 25, exiting the pad through the outflow tube 4 via the outlet 6. The coolant may comprise alcohol, water or any other material that remains in its fluid phase between the temperature of about 30 and 50° F. In another embodiment, the coolant contained in the cooling pad may be maintained at a slightly elevated temperature which is also been shown to be effective in stimulating wound healing and beneficial in the event of free tissue transfer (free flaps).

As shown in FIG. 3, a cooling supply may be connected to the cooling pad via the inflow tubing 5 and outflow 4. Cooling supply may further comprise a cooling unit 33. This cooling unit 33 may contain a reservoir for coolant; means for refrigeration, a control 31 for adjusting the temperature of the coolant exiting the reservoir, and means for circulating said coolant through said cooling unit, inflow tubing, inner chamber, and outflow tubing, such as a motor or pump. The pump must generate enough fluid pressure to exceed the forces of negative pressure created by the vacuum source, ensuring constant flow of coolant. In another embodiment, the cooling pad may be attached to upper side of the drape, over the wound site. In this embodiment, the cooling pad will be replaced with new one to maintain the desired temperature over the wound. This embodiment of the invention, allows the wound to be treated without being attached to a cooling supply and thus convenient for patient transport.

According to FIG. 8, certain embodiments provide for a wound contact layer 41 to be placed over the wound site 9. Preferably, the wound contact layer 41 can be a thin, flexible material which will not adhere to the wound site or the exposed viscera in close proximity. For example, polymers such as polyurethane, polyethylene, polytetrafluoroethylene, or blends thereof may be used. In one embodiment, the wound contact layer is permeable. For example, the wound contact layer 41 can be provided with openings 42, such as holes, slits, or channels, to allow the removal of fluids from the wound site 9 or the transmittal of negative pressure to the wound site 9. The wound contract layer may be placed between said wound and said cooling pad/drape to prevent overgrowth of wound tissue.

Referring to FIGS. 3 and 8, certain embodiments of the wound treatment system of this invention may also use one or more porous pad 21, which can be disposed over the wound contact layer 41, the cooling pad 22 or directly over the wound site. This pad 21 can be constructed from a porous material, for example foam, that is soft, resiliently flexible, and generally conformable to the wound site 9. The porous pad may comprise a porous sheet (such as a gauze), a foam screen (sponge) or any open cell foam. It may be made, for example, of a polymer. Suitable foams include foams composed of, for example, polyurethane, silicone, and polyvinyl alcohol. Preferably, this pad 21 can channel wound exudate and other fluids through itself when negative pressure is applied to the wound. Some pads 21 may include preformed channels or openings for such purposes. In certain embodiments, the pad 21 may have a thickness between about one inch and about two inches. The pad may also have a length of between about 16 and 17 inches, and a width of between about 11 and 12 inches. In other embodiments, the thickness, width, and/or length can have other suitable values. It may even be incorporated as a part of the cooling pad (FIG. 2). Additional filler materials may be included in the porous pad to absorbed excess exudates fluids from the wound. Such filler materials may comprise sponge, gauze pad, or gel materials.

As shown in FIG. 3, the outflow (exudates tubing) 2 connected a vacuum source 35, which produce a reduced pressure. The vacuum source has means for adjusting the reduced pressure applied to the wound.

The vacuum source may further contain or be connected to a collection storage 32 for collecting fluid aspirated from the wound. This collection storage may be a container or an expandable bag. Markings may be made on the collection device to provide indication 37 as to the amount of exudates collected. The collection storage may be an aspirating container connected along the tubing between the vacuum system and the drape (reservoir underneath the drape). There may be an additional halting means between the collection storage and the drape, such as a floatation valve, which can stop the application of reduced pressure to the wound when the fluid in the collection storage exceeds a predetermined quantity. A filter may also be inserted between drape and the collection storage to prevent odor and block waste materials from enter the tubing.

In an embodiment, as shown in FIGS. 1-3 and 8, once a wound is treated a wound contact layer is placed on the wound, which may be followed by a cooling pad with or without one more porous pad and covered with a substantially impermeable drape. Alternatively, the substantially impermeable drape may be placed over the wound directly, or over a cooling pad/contract layer/porous pad, sealing it to the healthy tissues surrounding the wound creating a substantially airtight water tight reservoir. The drape may be sealed to the healthy tissue via adhesive applied to the edge of the drape, or by adhesive tapes or elastics. In another embodiment, the cooling pad is attached to the outside the drape over the wound site after the wound is covered and the drape sealed. Tubing may then be used to connect the fluid port with the vacuum source. The inlet and outlet of the cooling pad may also be connected to the cooling unit via tubing. Once set up, both the vacuum source and the cooling unit are turned to desired levels to provide reduced pressure and localized cooling the wound. In another embodiment, the cooling pad is not connected to a cooling unit but is replaced with a new cooling pad periodically to maintain a desired temperature over the wound site.

EXAMPLE 1

Localized Cooling will Decrease Bacterial Load in a Soft Tissue Infection

A total of 42 rats (Harlan Sprague Dawley) were used for this study. All animals were quarantined, fed a standard diet and observed for seven days to ensure good health. The procedures were conducted in compliance with the Animal Welfare Act and the Guide for Care and Use of Laboratory Animals. The rats were anesthetized by intraperitoneal injections of 1000-1250 mg/Kg of urethane. A rectal temperature probe was inserted into each animal and remained in place until the subject was euthanized. Core temperatures were recorded prior to bacterial inoculation and then hourly over the ensuing eight hours.

The rats were randomly divided into three groups. Subjects in Group I (18) were inoculated and exposed to the localized cooling. Those in Group II (18 animals) were inoculated only. The animals in Group III (6) were simply placed under anesthesia, receiving no inoculation or exposure to the cooling blanket. A 3 cm×3cm area of skin between the scapulae was shaved and prepped with a surgical cleaning solution. A solution of $S.$ $aureus$ in 1 ml sterile saline was then injected into the subdermal adipose tissue for those animals in Groups I and II.

Immediately following inoculation of Group I, the rats were placed supine on a 50 degree Fahrenheit cooling pad (ThermoTek Inc., Flower Mound, Tex.). A heated surgical table and surgical warming blanket (Bair Hugger, Arizant Healthcare Inc., Eden Prairie, Minn.) were employed to prevent systemic hypothermia. Eight hours later, subjects in Group I and II were euthanized by an intraperitoneal overdose of Pentobarbital sodium (150 mg/kg). Following euthanasia, a 1.5 cm×1.5 cm area of skin was hinged open on three sides exposing the subdermal tissue. The incision was centered on the previous site of inoculation and performed under sterile technique. The underlying tissue, including the subdermal adipose tissue and superficial fascia, was excised and placed into a randomly numbered sterile container.

Samples were immediately homogenized in 2 ml of an appropriate growth medium by the laboratory members in the animal care facility. A 0.001 ml aliquot was inoculated onto duplicate 5% Sheep's Blood Agar Plates (BAP). The plates were transported immediately to the laboratory and incubated at 35 degrees Celsius in 5% carbon dioxide overnight. Following incubation, colony counts were performed and averaged to determine the number of colony forming units (CFU) per ml for each group. These data were then compared to the initial inoculum CFU.

The specimen number and treatment group were recorded by the investigators. Laboratory members were blinded as to which group received the cooling intervention. The animals in the Group III, uncooled and non-inoculated, were given time to recover from anesthesia. Any animal subject that expired prior to euthanasia was not included in the study.

Statistical analysis using the student's t-test was done to show any significant differences in bacterial colony counts and core temperature between the two groups. Forty-two rats were used for the study. One animal from the Group I, four animals from Group II and one animal from Group III expired before the end of the protocol. Data from these animals was excluded from the analysis. The remaining animals completed the study (FIG. 4). Bacterial colony counts from two animals in Group I and three animals in Group II were insufficient for accurate quantification and thus were excluded. This left 15 animals in Group I, 11 animals in the Group II and five animals in the Group III for analysis.

The average CFUs were significantly lower after localized cooling when compared to the control group ($1.74 \times 10^7$ vs. $2.17 \times 10^8$, respectively; p=0.041) (FIG. 5). Hourly temperature measurements were recorded (FIG. 6). The difference in temperature change from baseline between Groups I and II was statistically significant at all time points (p<0.01). The rats in group I demonstrated a statistically significant drop in core temperature from baseline from hours 3 to 8 (p<0.01) reaching the largest temperature decrease of 1.6° Celsius at hour 8.

The treatment of complex contaminated extremity wounds has continued to evolve, allowing for limb salvage in many cases where, in the past, amputation would have been the only option. The most common bacteria isolated from patients with open fractures have been gram positive organisms, more specifically Staphylococcus species. The need for prompt surgical debridement, skeletal stabilization, and intravenous antibiotics is well established. Localized cooling has played a large role in orthopedics, primarily due to its analgesic and anti-inflammatory properties. The application of a cooling pad alters the temperature in the affected area, shifting it out of the optimal zone for bacterial reproduction, significantly decreasing bacterial growth.

Although these results are encouraging, there are several other issues that need to be investigated. The small limb size of the rat limits the ability to reproducibly create a soft tissue extremity wound and accurately place the cryotherapy pad.

However, by inoculating the back of the animal and applying the cooling pad to the trunk, the risk for core hypothermia was substantially increased. Our localized cooling group displayed a core temperature decrease of only 1.6° Celsius. Although this value is statistically different from the baseline, it is unclear whether this small drop in temperature might impede the ability of the immune system to fight infection.

While the decrease in bacterial load was statistically significant, it is unknown whether this drop is clinically relevant. The interval between inoculation and tissue harvest was eight hours, a moderately short incubation time. In a level 1 trauma patient with open fractures, interventions such as negative pressure wound therapy are typically left in place for 48 to 72 hours between evaluations of wounds. Unfortunately, our data cannot be precisely extrapolated to these longer time intervals.

EXAMPLE 2

Validation of Localized Hypothermia Therapy in Goat Open Fracture Model

A validated goat open fracture model is employed to measure the effects of localized hypothermia on bacterial growth. The study group consisted of 6 female African Boer goats. After placing the animal under general endotracheal intubation, and performing a sterile prep and drape of both forelimbs, an 8×5 cm flap of skin was raised over the mid forelimb to later be sewn back into place. The tissue was then dissected down to expose a 5×5 cm flap of periosteum.

Electrocautery was utilized to incise, elevate and remove the flap of periosteum and obtain hemostasis for any exposed musculature of the anterior compartment of the forelimb. A 4 mm burr was used to decorticate the exposed cortical hone, creating punctuate bleeding. A through and through fracture was not created. Kelly clamps were placed onto the muscles of the anterior compartment and left in place for 3 minutes. In this model we have simulated an open fracture of the tibia with concurrent thermal and crush injury, which most accurately represents the types of extremity injury seen from soldiers returning from theater. After obtaining thorough hemostasis, 1 ml of S. Aureus Xe 29, a bioluminescent strain, containing 10 to the eighth aliquot of bacteria, was spread over the surface of the surgical site. Once the contamination was completed, a baseline image was obtained with a photon counting camera (Photek HRPCS-218, 18 mm Photon Counting Camera & System with ICCD118 camera Sydor Instruments LLC, Rochester, N.Y.). The angle and distance from the wound bed were controlled by mounting the camera to an Xray gantry and performing the surgery on a radiographic table. After imaging, a temperature probe was passed through the skin, into the surgical site and then sewn into position. The wound was then closed in an air tight running fashion with 4.0 nylon suture and sealed with Tega-derm. This same procedure was repeated on the opposite extremity. The animal was recovered and then placed in a suspension sling. Utilizing a cryotherapy cooling unit (Thermo-tek), capable of delivering a constant flow of cooled fluid at a regulated temperature, a cooling pad was randomly applied and secured to one of the goat forelimbs with Coban wrap. The temperature on the cooling unit was set to 40 degrees Fahrenheit. The other forelimb was utilized as the control. The animal was maintained under one to one observation for 48 hours, monitoring core and wound bed temperatures via thermal probes. Appropriate pain control and sedation were maintained throughout the testing period. At 48 hours, the cooling pad was removed. Once the temperature of the wound bed was restored to the temperature of the control limb, the animal was euthanized and returned to the surgical suite. Sutures were removed and repeat imaging was performed. At the conclusion of the imaging, cultures were obtained for quantization of colony forming units. This data will be subjected to statistical analysis. The results show at the time of the inoculation, the bacteria counts and bioluminescence in both control and treatment groups are about the same. However, a significant decrease (p<0.03) in photon emission is found in limbs that received localized cooling when compared to the control limb. See FIG. 7 and Table 1. A 100 fold increase in colony forming units was found in the control limb as compared to the cooled limb (Table 2). This was not significant at p<0.1. Additional testing of at least two more animals is to be undertaken Electrocautery was utilized to incise, elevate and remove the flap of periosteum and obtain hemostasis for any exposed musculature of the anterior compartment of the forelimb. A 4 mm burr was used to decorticate the exposed cortical bone, creating punctuate bleeding. A through and through fracture was not be created. Kelly clamps were placed onto the muscles of the anterior compartment and left in place for 3 minutes. In this model we have simulated an open fracture of the tibia with concurrent thermal and crush injury, which most accurately represents the types of extremity injury seen from soldiers returning from theater. After obtaining thorough hemostasis 1 ml of S. Aureus Xe 29, a bioluminescent strain, containing 10 to the eighth aliquot of bacteria, was spread over the surface of the surgical site. Once the contamination was completed, a baseline image was obtained with a photon counting camera (Photek HRPCS-218, 18 mm Photon Counting Camera & System with ICCD118 camera Sydor Instruments LLC, Rochester, N.Y.). The angle and distance from the wound bed were controlled by mounting the camera to an Xray gantry and performing the surgery on a radiographic table. After imaging, a temperature probe was passed through the skin, into the surgical site and then sewn into position. The wound was then closed in an air tight running fashion with 4.0 nylon suture and sealed with Tega-derm. This same procedure was repeated on the opposite extremity. The animal was recovered and then placed in a suspension sling. Utilizing a cryotherapy cooling unit (Thermo-tek), capable of delivering a constant flow of cooled fluid at a regulated temperature, a cooling pad was randomly applied and secured to one of the goat forelimbs with Coban wrap. The temperature on the cooling unit was set to 40 degrees Fahrenheit. The other forelimb was utilized as the control. The animal was maintained under one to one observation for 48 hours, monitoring core and wound bed temperatures via thermal probes. Appropriate pain control and sedation were maintained throughout the testing period. At 48 hours, the cooling pad was removed. Once the temperature of the wound bed was restored to the temperature of the control limb, the animal was euthanized and returned to the surgical suite. Sutures were removed and repeat imaging was performed. At the conclusion of the imaging, cultures were obtained for quantization of colony forming units. This data will be subjected to statistical analysis. The results show at the time of the inoculation, the bacteria counts and bioluminescence in both control and treatment groups are about the same. However, a significant decrease (p<0.03) in photon emission is found in limbs that received localized cooling when compared to the control limb. See FIG. 7 and Table 1. A 100 fold increase in colony forming units was found in the control limb as compared to the cooled limb (Table 2). This was not significant at p<0.1. Additional testing of at least two more animals is to be undertaken

TABLE 1 photon emission in open fracture goat model using cryotherapy.

| Goat Number | 1 | 2 | 3 | 4 | 5 | 6 | Avg |
|---|---|---|---|---|---|---|---|
| Cool | 1602 | 881 | 778 | 505 | 469 | 320 | 759.1666667 |
| Control | 1630 | 1723 | 1300 | 531 | 345 | 398 | 987.8333333 |
| Cool 48 h | 2268 | 2510 | 1539 | 919 | 273 | 514 | 1337.166667 |
| Control 48 h | 334403 | 161191 | 119809 | 116617 | 17298 | 60067 | 134897.5 |

TABLE 2

Quantitative Cultures

| Goat Number | 1 | 2 | 3 | 4 | 5 | 6 | Avg |
|---|---|---|---|---|---|---|---|
| Cool (CFU's) initial | $5.8 \times 10^8$ | $7.0 \times 10^8$ | $1.8 \times 10^8$ | $1.4 \times 10^8$ | $1.9 \times 10^8$ | $1.7 \times 10^8$ | $3.27 \times 10^8$ |
| Control (CFU'S) initial | $5.8 \times 10^8$ | $7.0 \times 10^8$ | $1.8 \times 10^8$ | $1.4 \times 10^8$ | $1.9 \times 10^8$ | $1.7 \times 10^8$ | $3.27 \times 10^8$ |
| Cool 48 h (CFU's) | $3.6 \times 10^3$ | $4.6 \times 10^3$ | $5.3 \times 10^4$ | $1.0 \times 10^2$ | N/A | $7.6 \times 10^4$ | $2.75 \times 10^4$ |
| Control 48 h (CFU's) | $8.9 \times 10^4$ | $3.9 \times 10^5$ | $2.5 \times 10^6$ | $4.2 \times 10^6$ | $1.0 \times 10^6$ | $1.0 \times 10^7$ | $3.03 \times 10^6$ |

PROPHETIC EXAMPLE 3

Validation of Treatment Method Against Traditional NWPT Treatment

A validated goat open fracture model is employed to measure the effects of localized hypothermia on bacterial growth. The study group consisted of 6 female African Boer goats. After placing the animal under general endotracheal intubation, and performing a sterile prep and drape of both forelimbs, an 8×5 cm flap of skin was raised over the mid forelimb to later be sewn back into place. The tissue was then dissected down to expose a 5×5 cm flap of periosteum. Electrocautery was utilized to incise, elevate and remove the flap of periosteum and obtain hemostasis for any exposed musculature of the anterior compartment of the forelimb. A 4 mm burr was used to decorticate the exposed cortical bone, creating punctuate bleeding. A through and through fracture was not created. Kelly clamps were placed onto the muscles of the anterior compartment and left in place for 3 minutes. In this model we have simulated an open fracture of the tibia with concurrent thermal and crush injury, which most accurately represents the types of extremity injury seen from soldiers returning from theater. After obtaining thorough hemostasis, 1 ml of S. Aureus Xe 29, a bioluminescent strain, containing 10 to the eighth aliquot of bacteria, was spread over the surface of the surgical site. Once the contamination was completed, a baseline image was obtained with a photon counting camera (Photek HRPCS-218, 18 mm Photon Counting Camera & System with ICCD118 camera Sydor Instruments LLC, Rochester, N.Y.). The angle and distance from the wound bed were controlled by mounting the camera to an Xray gantry and performing the surgery on a radiographic table. After imaging, a temperature probe was passed through the skin, into the surgical site and then sewn into position. The wound was then closed in an air tight running fashion with 4.0 nylon suture and sealed with Tega-derm. This same procedure was repeated on the opposite extremity. The animal was recovered and then placed in a suspension sling. Animal will received negative pressure wound therapy on one limb and a combination of cryotherapy and negative pressure on the other limb. The temperature on the cooling unit was set to 40 degrees Fahrenheit. Using rectal thermometers and skin probes, data on core body temperature and local temperatures of the forelimb receiving the intervention are collected. Following wound inoculation, a baseline reading of photon emission are obtained with a specialized photon counting camera (Photek HRPCS-218, 18 mm Photon Counting Camera & System with ICCD118 camera Sydor Instruments LLC, Rochester, N.Y.).

After application of the intervention, the animals recover from anesthesia and return to the housing area. In order to protect the equipment from destruction and keep the wounds undisturbed, the goats are maintained in suspension slings under one to one observation and sedation for 48 hours. After 48 hours of incubation, the goats are euthanized and both forelimb wounds are subjected to a second reading with the photon counting camera. The change in photon emission from the initial inoculation, based on the bioluminescence radiating from the wound bed, provided a comparison of bacterial growth for the control and intervention limbs. After photon emission testing, quantitative cultures will be obtained through random sampling of the wound bed. This data will be subjected to statistical analysis.

REFERENCES

1. Hospenthal D R, Murray C K, Andersen R C, Blice J P, Calhoun J H, Cancio L C, Chung K K, Conger N G, Crouch H K, D'Avignon L C, Dunne J R, Ficke J R, Hale R G, Hayes D K, Hirsch E F, Hsu J R, Jenkins D H, Keeling J J, Martin R R, Moores L E, Petersen K, Saffle J R, Solomkin J S, Tasker S A, Valadka A B, Wiesen A R, Wortmann G W, Holcomb J B. Guidelines for the Prevention of Infection After Combat-related Injuries. Journal of Trauma. 2008; 64:S211-S220.

2. Leaper D. Effects of Local and Systemic Warming on Postoperative Infections. Surgical Infections. 2006; 7:S101-S103.
3. Melling A C, Baqar A, Scott E M, Leaper D J. Effects of preoperative warming on the incidence of wound infection after clean surgery: a randomised controlled trial. The Lancet. 2001; 358:876-80.
4. Torossian A, Ruehlmann S, Middeke M, Sessler D I, Lorenz W, Wulf H F, Bauhofer A. Mild preseptic hypothermia is detrimental in rats. Critical Care Medicine. 2004; 32:1899-1903.
5. Kurz A, Sessler D I, Lenhardt R. Perioperative normothermia to reduce the incidence of surgical-wound infection and shorten hospitalization. The New England Journal of Medicine. 1996; 334:1209-15.
6. Sheffield C W, Sessler D I, Hunt T K, Scheuenstuhl H. Mild hypothermia during halothane-induced anesthesia decreases resistance to *Staphylococcus aureus* dermal infection in guinea pigs. Wound Repair and Regeneration. 1994; 2:48-56.
7. Huet O, Kinirons B, Dupic L, Lajcunie E, Mazoit J X, Benhamou D, Vicaut E, Duranteau J. Induced mild hypothermia reduces mortality during acute inflammation in rats. Acta Anaesthesiologica Scandinavica. 2007; 51:1211-1216.
8. L'Her E, Amerand A, Vettier A, Sebert P. Effects of mild induced hypothermia during experimental sepsis. Critical Care Medicine. 2006; 34:2621-2623.
9. Deal D N, Tipton J, Rosencrance E, Curl W W, Smith T L. Ice Reduces Edema: A Study of Microvascular Permeability in Rats. The Journal of Bone and Joint Surgery. 2002; 84A:1573-8.
10. Hopkins J T, Ingersoll C D, Edwards J, Klootwyk T E. Cryotherapy and Transcutaneous Electric Neuromuscular Stimulation Decrease Arthrogenic Muscle Inhbition of the Vastus Medialis After Knee Joint Effusion. Journal of Athletic Training. 2001; 37(1):25-31
11. Ohkoshi Y, Ohkoshi M, Nagasaki S, Ono A, Hashimoto T, Yamane S. The Effect of Cryotherapy on Intraarticular Temperature and Postoperative Care After Anterior Cruciate Ligament Reconstruction. The American Journal of Sports Medicine. 1999; 27:357-62.
12. Saito N, Horiuchi H, Kobayashi S, Nawata M, Takaoka K. Continuous Local Cooling for Pain Relief Following Total Hip Arthroplasty. The Journal of Arthroplasty. 2004; 19:334-7.
13. Schaser K, Disch A C, Stover J F, Lauffer A, Bail H J, Mittlmeier T. Prolonged Superficial Local Cryotherapy Attenuates Microcirculatory Impairment, Regional Inflammation, and Muscle Necrosis After Closed Soft Tissue Injury in Rats. The American Journal of Sports Medicine. 2007; 35:93-102.
14. Murray C K. Epidemiology of Infections Associated With Combat-related Injuries in Iraq and Afghanistan. Journal of Trauma. 2008; 64:S232-8.
15. Murray C K, Hsu J R, Solomkin J S, Keeling J J, Andersen R C, Ficke J R, Calhoun J H. Prevention and Management of Infections Associated With Combat-related Extremity Injuries. Journal of Trauma. 2008; 64:S239-S251.

What is claimed is:
1. A system to promote the healing of a wound, comprising:
(a) a flexible drape sized to seal in a wound site, and adapted to maintain a substantial airtight watertight reservoir over the wound site, wherein said flexible drape has a resealable connector in the middle;
(b) a cooling pad, placed over the wound site and is in fluid communication with a coolant supply which has a control for temperature of outgoing coolant; and
(c) a reduced pressure mechanism including
(i) a control unit disposed within a housing, the control unit including a vacuum source; and
(ii) a collection storage having an interior wall defining an internal chamber in fluid communication with the vacuum source of the reduced pressure mechanism and with said reservoir over the wound site through a vacuum port for collecting exudates removed from the wound site under influence of the vacuum source; wherein said reduced pressure mechanism maintains a pressure from about 2 in. Hg below atmospheric pressure to about 7 in. Hg below atmospheric pressure at the reservoir and wherein said coolant is maintained at a temperature from about 30° F. to about 50°.
2. The system of claim 1, further comprising a contacting layer adapted to prevent overgrowth of wound tissue, said contacting layer is placed directly over the wound site.
3. The system of claim 2, wherein said contacting layer is a screen.
4. The system of claim 3, wherein said screen is made of a material selected from the group consisting of polyurethane, polyethylene, polytetrafluoroethylene, and blends thereof.
5. The system of claim 1, further comprising one or more planar porous pad suitable for the transmission of negative pressure to the wound site and provided with a thickness less than its width and length.
6. The system of claim 5, wherein said porous pad is made of materials selected from the group consisting of a porous sheet, a foam screen, a sponge, open cell foam and a combination thereof.
7. The system of claim 5, wherein said porous pad is placed directly or indirectly over the wound site and under the drape.
8. The system of claim 1, wherein said flexible drape is made of a material selected from the group consisting of polyethylene, polypropylene, polyurethanes, polysiloxanes, polyamides, polyesters, other copolymers and mixtures thereof.
9. The system of claim 1, wherein said flexible drape is configured to be sealed to healthy tissue surrounding the wound site by applying an adhesive material applied to the peripheral of said drape.
10. The system of claim 1, wherein said flexible drape is configured to be sealed to the healthy tissue surrounding the wound site by adhesive tape.
11. The system of claim 1, wherein said vacuum port is connected to said reservoir over the wound site using flexible tubing, allowing fluid communication between the vacuum and the reservoir.
12. The system of claim 11, wherein
(a) a proximal end of said tubing is connected to the resealable opening on said drape; and
(b) a distal end of said tubing is connected to the vacuum port.
13. The system of claim 12, wherein said tubing is connected to said resealable opening using a connector.
14. The system of claim 12, wherein at least a segment of said tubing is embedded underneath said drape.
15. The system of claim 1, wherein said control unit can adjust the reduced pressure applied to the wound.

16. The system of claim 1, wherein said collection storage further comprises means for halting said application of reduced pressure to the wound when said fluid exceeds a predetermined quantity.

17. The system of claim 12, wherein said collection storage comprising an aspirating container connected along said tubing between said control unit and said flexible drape.

18. The system of claim 16, wherein said means for halting comprising a flotation valve within said collection storage for blocking the flow of fluid when a predetermined amount of fluid is collected within said storage.

19. The system of claim 11, wherein said collection storage comprising indicators showing the amount of fluid collected inside said collection storage.

20. The system of claim 1, wherein said collection storage is an expandable chamber.

21. The system of claim 1, further comprising at least one filter interposed between said reservoir and said vacuum source.

22. The system of 21, wherein said filter is hydrophobic filter.

23. The system of claim 21, wherein said filter is an odor vapor filter.

24. The system of claim 1, wherein said cooling pad is water-proof pouch having a continuous, outer surface, said outer surface forming an inner chamber containing a coolant.

25. The system of claim 24, wherein at least a portion of said pouch have openings, allowing aspired fluid from the wound site to pass through said cooling pad.

26. The system of claim 24, wherein said inner chamber of said cooling pad is adapted to allow coolant to circulate through the entire inner chamber.

27. The system of claim 24, wherein said coolant comprising of materials selected from the group consisting of alcohol, water, gel and other cooling fluid.

28. The system of claim 1, wherein said coolant supply comprising:
(a) a cooling unit capable of circulating coolant at a pressure exceeding the negative pressure of the vacuum source, and
(b) an inflow tubing and an outflow tubing, both tubing operably connected to and in fluid communication with said cooling unit and said inner chamber of said cooling pad.

29. The system of claim 28, wherein said cooling unit further comprising
(a) means for changing the temperature of said coolant;
(b) means for adjusting the temperature of said coolant and
(c) means for circuiting said coolant through said cooling unit, inflow tubing, inner chamber, and outflow tubing.

30. The system of claim 26, wherein said coolant is maintained at higher than normal body temperature, which aids wound healing after free tissue transfer.

* * * * *